US006726896B2

(12) United States Patent
Tait

(10) Patent No.: US 6,726,896 B2
(45) Date of Patent: Apr. 27, 2004

(54) STOOL MARKER

(76) Inventor: Kevin Tait, 46A Woonona Ave., Wahroonga NSW 2076 (AU)

( * ) Notice: Subject to any disclaimer, the term of this patent is extended or adjusted under 35 U.S.C. 154(b) by 0 days.

(21) Appl. No.: 09/800,076

(22) Filed: Mar. 5, 2001

(65) Prior Publication Data

US 2001/0036442 A1 Nov. 1, 2001

(30) Foreign Application Priority Data

Mar. 7, 2000 (AU) .............................................. PQ6055

(51) Int. Cl.[7] .............................................. A61K 49/00
(52) U.S. Cl. ...................................... 424/9.41; 424/9.4
(58) Field of Search ................................ 424/9.4, 9.41, 424/9.411

(56) References Cited

U.S. PATENT DOCUMENTS

| | | | | |
|---|---|---|---|---|
| 3,935,099 A | * | 1/1976 | Weaver et al. ................. | 210/43 |
| 4,120,946 A | * | 10/1978 | Queuille et al. .............. | 424/9.4 |
| 4,692,325 A | * | 9/1987 | Kritzler et al. .............. | 424/9.4 |
| 5,460,798 A | | 10/1995 | Barnett ........................ | 424/9.4 |
| 5,466,440 A | * | 11/1995 | Ruddy et al. ............. | 424/9.711 |
| 5,518,711 A | | 5/1996 | Tonariya et al. ......... | 424/9.411 |
| 6,001,334 A | * | 12/1999 | Hirai ........................ | 424/9.411 |

FOREIGN PATENT DOCUMENTS

| | | |
|---|---|---|
| EP | 0 609 587 A2 | 8/1994 |
| EP | 0 620 012 A1 | 10/1994 |
| JP | 08217697 A | 8/1996 |
| WO | WO 97/30736 | 8/1997 |

OTHER PUBLICATIONS

A. K. Hara, et al., "Detection of Colorectal Polyps by Computed Tomographic Colography: Feasibility of a Novel Technique", GASTROENTEROLOGY, Saunders, Philadelphia, PA, US, vol. 110, No. 1, Jan. 1996, pp. 284–290.

*Virtual colonoscopy: State–of–the–art alternative to total colon evaluation,* Helen M. Fenlon et al., *Diagnostic Imaging,* Nov. 1998, pp. 118–123 and 193.

*CT colonography: Spiraling into the future,* C. Daniel Johnson, M.D., *Applied Radiology,* Sep. 1999, pp. 16–20.

\* cited by examiner

*Primary Examiner*—Michael G. Hartley
(74) *Attorney, Agent, or Firm*—Weingarten, Schurgin, Gagenbin & Lebovici LLP

(57) ABSTRACT

A stool marker formulation for oral administration and suitable for use in CT Colography including a material adapted to provide marked stool which has a modified response to radiation relative to unmarked stool. Radiologically scanning the colon of a patient treated to produce marked stool produces data which can be manipulated to provide a representation of the colon including where present, a polyp. The active ingredient is preferably barium sulfate which has been destabilised to reduce its resistance to flocculation.

19 Claims, No Drawings

STOOL MARKER

FIELD OF THE INVENTION

The present invention relates to methods of rendering an image of an organ, in particular a colon, in a manner suitable for detecting colon cancer using methods such as CT Colography, and to compositions suitable for use in these methods.

BACKGROUND

In western-style communities, colorectal cancer is the third most common form of cancer and has the second highest death rate. Over 80% of colorectal cancers originate as a polyp, which, unless there has been a family history of colon cancer, tend not to develop until the patient reaches 50 years of age. Removal of the polyp will terminate the risk of cancer originating at that site. The development from polyp to cancer is slow, usually requiring about ten years. Because of these factors, adequate screening of the "at-risk" population for colorectal cancer will have a major effect on prevention.

Techniques exist at present that can locate colonic polyps with high accuracy. Amongst the most widely used method of detection is radiological examination. However, radiological examinations of soft-tissues, such as the colon, are limited by their poor X-ray absorption characteristics. Without artificial enhancement, such tissues are poorly imaged, and a contrast agent, which strongly interacts with X-rays, such as barium sulfate, is required.

The most commonly employed radiological technique is the double contrast barium enema. This requires a strictly regulated diet, together with the administration of extremely potent laxative products, for up to 48 hours prior to the examination to produce the so-called "fully prepared colon". Barium sulfate is then placed in the patient's rectum and colon via the anus prior to radiological examination. The barium enema examination typically carries some stigma, is uncomfortable, and word of mouth accounts usually ensure that a patient presenting for the first time already has an extensive knowledge of the unpleasantness that lies in store.

Colonoscopy is a popular, if more expensive, alternative to the barium enema but which still requires a strict dietary and laxative regime similar to the barium enema to produce the fully prepared colon. Colonoscopy requires that the patient be heavily sedated during the procedure as it is substantially more uncomfortable and invasive than a barium enema. It also entails substantially more expense to the community, and inconvenience to the patient, who may require hospitalisation. Colonoscopy also has a fairly high risk of patient injury about 1 in 7000 patients suffering a perforation of the colon and about 1 in 50,000 dying from the procedure as a result of complications to the perforation or adverse reactions to the anaesthetic.

An alternative diagnostic technique has been introduced that is far less problematic for the patient and should increase the likelihood of acceptance by the general public. This technique has a variety of names, including Virtual Colonoscopy, Virtual Colography, CT Colography and CT Colonography. It requires the patient to undergo a CT scan of the abdomen. Subsequent image reconstruction allows examination of the colon in order to detect polyps. This technique has only become possible with the recent arrival of helical CT scanners, in which the data acquisition takes place in a continuous process (unlike previous scanners which acquired data in consecutive slices), together with high performance work stations capable of rapidly rendering 3D-views into useful medical information.

A number of trials have confirmed the feasibility of CT Colography as an accurate screening technique for colon cancer. However, this too has similar drawbacks to the other methods which may prevent it being widely used as a preventative tool against colon cancer.

Under normal circumstances the colon is heavily loaded with stool (faeces) at various stages of development. Faeces often has the same size and appearance as polyps in a CT scan, and in practical terms they are generally indistinguishable from each other.

Thus, to be effective, CT Colography requires patients to have a fully prepared colon by submitting to the same rigorous diet and laxative program used for Colonoscopy. Thus, while some of the discomfort and inconvenience of the previous procedures have been avoided, the requirement for a prepared colon has not minimised patient discomfort to the point that it will obtain high acceptance by the "at risk" population group.

The degree of discomfort and inconvenience of all the investigative techniques available to check for colonic polyps means that very much less than 10% of the "at risk" population have these examinations even once in their life, let alone at the five yearly frequencies advocated by various studies.

The above discussion of prior art is not to be construed as an admission with regard to the common general knowledge in Australia.

It is an object of the present invention to overcome or ameliorate at least one of the disadvantages of the prior art, or at least to provide a useful alternative.

DISCLOSURE OF THE INVENTION

According to a first aspect the invention provides a stool marker formulation for oral administration and suitable for use in CT Colography including a material adapted to provide marked stool, said marked stool having a modified response to radiation relative to unmarked stool.

Normally, the modified response to radiation is to render stool opaque to radiation.

In preferred embodiments, the material to render stool opaque to radiation is water insoluble, and most preferably is barium sulfate. However, other materials can be used, for example iodine compounds. Iodinated materials can be used provided these have been rendered into an insoluble form that passes through the gastrointestinal tract without being dissolved or metabolised. Suitable iodine compounds include for example: Iopanoic acid; Dionosil (propylidone); Hytrast, a mixture of Iopydol and Iopydone; Lipiodol; Iodipin; Iodochloral; Iophendylate; Ethiodol and other Iodinated vegetable oils or any polymeric material containing organically bound iodine atoms in sufficient quantity to achieve radio opacity.

Alternatively, the materials to render stool opaque to radiation can include finely divided particles of metals, metal oxides and metallic salts, for example bismuth, iron, platinum, gold, strontium and the like.

The stool marker formulation is ideally administered in an amount effective to differentiate stool from non-stool without rendering density or movement induced artefacts in the CT rendering of the stool. Thus, when barium sulfate is administered as the material to render stool opaque to radiation in liquid form, it does not exceed 3% wt per volume of the formulation. When the preferred dosage sizes of 200–250 mL are used, the absolute dosage of barium sulfate accordingly preferably does not exceed 6–7.5 g. A dosage of about 5 g has been found to be particularly useful. Liquid formulations containing barium sulfate in an amount of as low as 0.5 wt per volume (total around 1 g barium sulfate) may also be used. Employing too low a quantity of marker will of course prevent effective differentiation between marked and non-marked stool.

In an alternative but equally preferred embodiment, the barium sulfate may be administered in a solid form, to achieve the same total dosage and to provide marked stool. A solid dosage form of 5 g has been found particularly useful.

In highly preferred the stool marker formulations of the present invention, the material to render stool opaque to radiation is destabilised to ensure that the resistance to flocculation is minimised. Preferably, this destabilisation takes place by limiting the amount of ionic dispersants in the formulation and/or by the addition of flocculants.

It is also advantageous if the tendency for agglomeration of the individual active particles of the material to render stool opaque to radiation is inhibited before administration to the patient. This inhibition may takes place for instance by ensuring that the particles are separated during preparation of the formulation or prior to administration, using techniques such as high shear stirring or sonification.

The viscosity of the stool marker formulation may be altered as desired by using a compatible viscosity modifier. Preferably, the viscosity modifier does not behave as a protective colloid in respect of the material to render stool opaque to radiation.

The stool marker formulation may also include an anti-caking agent, or other pharmaceutical excipients, carriers, colourants, flavourants and the like, provided these are included in an amount which does not unduly adversely effect the functioning of the stool marker formulation.

According to a second aspect the invention provides a method of radiologically visualising the colon of a patient including the steps of:
  orally administering to a patient a marker to provide marked stool, said marked stool having a modified response to radiation relative to unmarked stool;
  radiologically scanning the colon of the patient to produce data; and
  manipulating the data to determine that portion of the data due to marked stool, to thereby provide a representation of the colon, including where present, a polyp.

Radiological visualisation may be for example by means of a CT scanner such as a helical scanner.

Preferably, the response of stool to radiation which is modified is to render it opaque to radiation. Manipulation of the data may, for instance involve subtraction of that portion of the data due to the marked stool, leaving a representation of the colon, including where present a polyp.

According to an third aspect, the invention provides a method of preparing a patient for a radiological examination including the step of administering to the patient a material to render stool opaque to radiation. The material is administered orally, preferably over the 24 to 48 hours preceding die radiological examination in four, six or more dosages, with around 5 g being administered per dose.

The term "dose", "dosage" and the like as used herein refers to the quantity administered to a patient at any one time.

BEST MODE OF PERFORMING THE INVENTION

Barium Sulfate preparations administered in various known techniques have as a common objective the preparation of what is in fact an in-situ "mould" of an organ which demonstrates the organ's shape, or surface characteristics.

While barium sulfate has been used to investigate gastrointestinal tract disease or as a marker to help define the anatomy of the GI tract, there have been no previous attempts to use barium sulfate to specifically image stool.

All previous uses of barium sulfate (and other radio opaque contrast materials) rely on the physico-chemical properties of the barium sulfate being stabilised to avoid coagulation and/or flocculation. Additives in previous formulations act as protective colloids in order to achieve this end Indeed, should these preparations coagulate in, for example, a barium meal or enema, the X-Ray image that is produced is one of "curdled milk" and the barium sulfate suspension ceases to be a faithful representation of the underlying tissue features. By contrast, in a preferred embodiment of the present invention, the stool marker of the present invention is designed to coagulate during its passage through the gastrointestinal tract. Surprisingly, this has been found by the present inventor to benefit efficient uptake into the stool.

When it is intended to modify stool to render it opaque to radiation, the stool marker formulation should include an opacifying material which is pharmacologically inert, and passes through the GI tract without being dissolved or metabolised. Most preferably, the formulation contains barium sulfate, however, iodine compounds and other compounds such as bismuth, iron, platinum, gold, strontium and the like may be used.

Some preferred formulations are shown in table 1.

TABLE 1

| Formula | Gastrovue (comparative example) | I | II | III | IV | V | VI |
|---|---|---|---|---|---|---|---|
| Active | Diatrizoate (Soluble) | $BaSO_4$ | $BaSO_4$ | $BaSO_4$ | $BaSO_4$ | $BaSO_4$ | $BaSO_4$ |
| % w/v | 1.6 | 3.0 | 1.2 | 0.86 | 0.94 | 1.16 | 1.20 |
| Anionic Dispersant Content | None | 0.038N | 0.056N | 0.147N | 0.059N | 0.032N | 0.007N |
| Flocculation resistance | Not applicable | 1 mL | 30 mL | 5 mL | 3 mL | 0.8 mL | 0.5 mL |
| Anti-caking agent | Not applicable | Smectite Clay | nil | Smecite Clay | Smectite Clay | Smectite Clay | Smectite Clay |
| Viscosity Modifier | None | Xanthan | Xanthan | Xanthan | Xanthan | Xanthan | HydrMC |

TABLE 1-continued

| Formula | Gastrovue (comparative example) | I | II | III | IV | V | VI |
|---|---|---|---|---|---|---|---|
| Performance (10 = perfect)** | | | | | | | |
| Right Colon | 0 | 6.2 | 1.5 | 3.8 | 5.5 | 7.3 | 9.0 |
| Left Colon | 0 | 8.8 | 6.0 | 6.0 | 6.8 | 9.8 | 9.5 |
| Artefacts | No | Some | No | No | No | No | No |

*Flocculation Resistance Test: Take an amount equivalent to 10% of a typical dose, such as 20.0 g of suspension or 0.25 g of powder, diluted to 50 mL water. Titrate with a solution of 3.0% w/v Ferrous Sulfate, acidified with the dilute sulphuric acid, to a pH of 5.0–5.5. The number of mL of titrant required before the suspension became coagulated is recorded. The higher the number, the greater is the sample resistance to flocculation by ionic species.
**Using optimum administration technique
HydrMC = hydroxypropyl methylcellulose Iodinated materials could also be used provided that these have been rendered into an insoluble form that passes trough the GI tract without substantial dissolution or metabolism. Table 1 shows a comparative test which uses a water-soluble marker compound (Gastrovue™). Iodinated materials could include Iopanoic acid, a water insoluble solid which is currently used to opacify the gallbladder, Dionisil (propylidone), a water-insoluble solid that has been used for bronchography, Hytrast, a mixture of Iopydol and Iopydone which is a water insoluble solid, Lipiodol, Iodipin, Iodochloral, Iophendylate and Ethiodol, which are Iodinated vegetable oils and any polymeric material which contains organically bound iodine atoms in sufficient quantity to be radio-opaque. In the case of all these iodinated compounds, the active material should be prepared in an aqueous suspension of finely divided material.

It is important that the active ingredient used in the stool marker be controlled. During incorporation into stool after administration, the material becomes concentrated. The CT scan and data reconstruction, ie after the subtraction of the stool signal, will suffer from artefacts if it is necessary to handle data from dense opacifications, especially where these are in motion during the scan, a situation which is inevitable if in the GI tract.

For example, the maximum concentration of barium sulfate in the suspension administered to the patient should not be more than 3% wt per volume, and is preferably in the range of 0.5–1.5% wt per volume.

For other potential contrast agents, the amount used will be directly dependent on the atomic wt of the marking agent. When such an alternative contrast material agent is chosen, the formula to produce a radio-opacity with this alternate material, comparable to that produced by barium sulfate is given by the formula below and is:

$$\% \ w/vM = \% \ w/v \ BaSO_4 \times 137.33/233.43 \times 137.33/At. \ Wt. \ of \ M$$

where:

M is the alternate atom to be used as the radio-opaque material, for eg, Iodine, Iron, Bismuth or Platinum; and % w/v $BaSO_4$ is a concentration of barium sulfate whose radio-opacity is being matched.

Ideally, the stool marker is administered as an aqueous suspension, where the active is a water-insoluble solid, or as an emulsion, wherein the active is a fluid that is emulsified with water. Alternatively, the product can be formulated as a solid which can be converted into an aqueous form by the addition of water prior to administration to the patient.

Alternatively, the medication can be administered in solid form in which case it would need to have been formulated to ensure that the natural formations of the GI tract would render it into the required suspension/emulsion in the stomach and small bowel. In this latter case, if the solid administration is proceeded or followed by a fluid chaser, the relative amounts of each will be such as to comply with a requirement of less than 3% wt per volume barium sulfate, or the equivalent, and preferably 0.5–1.5% w/v barium sulfate or equivalent.

When these concentrations are used in conjunction with the dosage sizes exemplified below, of 200–250 mL, it will be appreciated that the amount of $BaSO_4$ present does not exceed 6–7.5 g. In typical patients, it is preferred if the total amount of $BaSO_4$ per dose does not exceed 5 g.

When relying on the body's natural fluids to supply the material required to form the suspension/emulsion, the formulation can be formulated in such a way that it ensures with sufficient predictability that the resultant suspension complies with the formula above.

As mentioned above, in vitro or in vivo, it is highly desirable that the flocculation resistance of the suspension/emulsion be very low. This is contrary to the objective of most preparations. It is certainly the exact opposite of the formulation objective used in the preparation of traditional barium sulfate based contrast agents.

Flocculation resistance is defined herein as the tendency for the individual suspension particles, or emulsion droplets, to repel each other and thereby resist coalescence.

Flocculation resistance can be measured by a number of techniques such as the measurement of electrophoretic mobility of the suspension, observation of phase separation in the case of emulsions, and titration with a flocculent, such as a solution of a highly charged ionic species, especially in the case of suspensions.

Flocculation resistance can be induced by altering the natural surface charge carried by the particle. In the case of aqueous suspensions of inorganic pigments such as barium sulfate, this can be achieved by increasing surface charge to such an extent that the particles become stabilised due to their mutual repulsion. This may be achieved by the addition of anionic materials such as citrates, polyphosphates and anionic polymers.

Alternatively, flocculation resistance may be achieved by the incorporation of protective colloids, the function of which have been described in the literature and are known to chemists. Typically, protective colloids are believed to adsorb to the particle surface, and provide a barrier to the interaction of highly charged flocculants with a solid surface. In particular, natural and synthetic hydrocolloids of anionic character (in pH regions of practical interest such as pH 4–10) all may perform as protective colloids for barium sulfate and are best avoided. These include, but are not limited to carmellose sodium, acacia, tragacanth, and alginates.

Thus, it would be expected that a successful stool marker should not include in substantial portion these substances where possible. Table 1 shows a number of stool marker formulations. It can be seen that the performance as a stool marker clearly improves as flocculation resistance decreases.

Further, Table 1 shows that the incorporation of a material to sensitise the suspension to flocculants is a positive step. Clays are particularly flocculation prone, and their incorporation into formulas, even those with relatively high contents of ionic dispersals, eg formula IV, produce unexpectedly low titration values with subsequent improvements in stool marker performance.

In the present specification, the flocculation resistance of candidate formulas have been determined by titrating a measured quantity with an acidified 3% w/v Ferrous Sulfate solution. Preferably, it can be seen that flocculation resistance will be less than 5 mL and preferably less than 1 mL of a 3% acidified Ferrous Sulfate solution. Where a material capable of performing as an anionic dispersant, for example citrate ion, is included into the formula, for example, for reasons of flavour enhancement or viscosity modification or preservation etc then the total concentration should be kept to a minimum, for example to less than 0.035N (gram-equivalent weights per L of suspension) and preferably less than 0.010N. Flocculation resistance is also reduced by the incorporation of sensitisers that are themselves inherently prone to flocculation, and which by their very presence transfers this desirable property to the entire formula.

Even though the concentration of the opacifying material may be controlled as described above, it is desirable to ensure that it remains as finely divided material right up to the point where it becomes incorporated into the stool. If, during its shelf life or during its transit through the GI tract, the active material particles become agglomerated into larger entities, these will appear as hyperdense areas in the CAT Scan image, and will create artefacts for the reasons discussed above.

Methods to prevent or slow this agglomeration process include:
- high shear dispersion to the suspension or emulsion at the point of manufacture or at the point of administration,
- conversion of highly dispersed suspensions into a powder form by spray drying, or similar methods, to produce a powder dosage form in which the active material has been coated with the dispersion aids such as viscosity modifiers and or anti-caking agents.
- the use of selected particle size which readily disperse with minimum agitation. Commercially available barium sulfate typically has a mean particle size (diameter) of around 1 micron, and unless treated by spray drying, or a similar process, cannot be dispersed unless subject to very high shear conditions. The use of barium sulfate of around 3 microns average diameter is, by contrast, readily dispersed by simple hand mixing, stirring and/or shaking and the like.
- incorporation of a viscosity increasing material, since the rate of agglomeration is reduced as the viscosity increases,
- the use of an anti-caking agent that becomes incorporated into any sediments formed by the active material if a solid. These anti-caking agents prevent the formation of very dense sediments that are very difficult to resuspend by hand agitation. By assisting easy re-suspension, such agents allow the reformation of well dispersed active material.

As mentioned above, to select an ideal viscosity modifying agent, one should not be chosen from among the very large number of ionic species, as these may adversely improve flocculation resistance by acting as protective colloids.

For suspensions of barium sulfate or other opacifying materials carrying a surface charge, possible choices for viscosity control include nonionic polymeric species, both natural and synthetic, and some compatible colloidal minerals and will include such materials as xanthan gum, hydroxypropylcellulose, hydroxybutylmethylcellulose, methylcellulose, propylene glycol alginate, pectin, and clays such as bentomite, hectorite, smectite and kaolin.

For anti-caking control of suspensions, choices include clays, colloidal silicone materials, amorphous silica, silica gels, and colloidal and anhydrous silica are preferred.

In order to opacify stool throughout the entirety of the colon, it has been found that the material should begin to be dosed 48 hours prior to the examination. Additionally, the administration of at least 6 spaced dosages, each of 200–250 mL of 1.2% suspension, or each of 2.4 g powder, gives substantially better results than 4 doses. Table 2 sets out the relative performance of various dosage/timing regimes. For liquid dosages, the stool marker is preferably made up in a minimum of 1200 mL of material in at least 6 evenly spaced dosages with at least one dosage early in the day of examination and another on the late evening preceding the examination.

As a general rule, regardless of whether the dosage form is administered as a suspension or solid (or a combination of the two), the total amount of barium solid administered in the six evenly spaced doses is equivalent to at least 14.4 g.

TABLE 2

ADMINISTRATION METHODS

| | Performance in: | |
|---|---|---|
| Dosage Regime | Right Colon | Left Colon |
| 24(2) | 5.5 | 4.3 |
| 24(4) | 6.8 | 6.0 |
| 48(4) | 6.8 | 8.0 |
| 48(6) | 9.0 | 9.5 | where:

24(2) means 225 mL doses given 7 am, 7 pm os day prior to day of examination
24(4) means 225 mL doses given 7 am, 7 pm, 12 pm od day prior to, and at 6 am on day of examination
48(4) means 225 mL doses given 7 am, 7 pm, 7 am, 7 pm of the two days prior to the day of examination
48(6) means 225 mL doses given 7 am, 7 pm, 7 am, 7 pm, 12 pm of the two days prior to the day of the examination, and at 6 am on day of examination Maximum Performance rating is 1

TABLE 3

PREFERRED FORMULA - SUSPENSION DOSAGE FORM
A preferred formula for a suspension dosage form is a ready-to-use suspension of barium sulfate, in which the required dispersion is achieved by high shear agitation during manufacture.

| Ingredient | Quantity |
| --- | --- |
| Purified Water | 1000 mL |
| Barium Sulfate | 12 g |
| Citric Acid Anhydrous | 0.3 g |
| Hydroxypropyl methylcellulose | 4.5 g |
| Smectite Clay | 7.5 g |
| Flavour, Sweetener, Preservatives | q.s. |

TABLE 4

PREFERRED FORMULA - SOLID DOSAGE FORM
A preferred formula for a solid dosage form is a ready-to-use powder, which may or may not be in tablet form

| Ingredient | Composition (% by weight) |
| --- | --- |
| Barium Sulfate | 95% |
| Smectite Clay | 2.0% |
| Xanthan Gum | 1.5% |
| Sodium Citrate | 0.1% |
| Flavour, Sweetener, Preservatives | q.s. |

The mixture may be presuspended in water and predried. Alternatively, the xanthan gum and citrate are dissolved in a minimum volume of water, and sprayed onto the barium sulfate while mixing. The mixture is allowed to dry while mixing takes place by moderate heating, or by drawing air through the powder.

The powder can be converted into tablets or gelatine capsules in accordance with normal formulating procedures. Each discrete dosage contains 600 mg of powder. At each sitting, consistent with the dosage regime described above, 4×600 mg tablets or capsules are administered.

Although the invention has been described with reference to specific examples, it will be appreciated by those skilled in the art that the invention may be embodied in many other forms.

The claims defining the invention are as follows:

1. A liquid stool marker formulation which renders stool opaque to radiation in CT colography, said formulation comprising:

from 0 to less than 0.035N ionic dispersants;
   0.5 to 3% w/v barium sulfate; and
   a flocculant to flocculate said radio opacifying agent, wherein 20 g of said liquid formulation diluted with water to 50 ml and titrated against 3.0% w/v ferrous sulfate at pH5.0–5.5 has a flocculation resistance of less than 5 ml.

2. A liquid stool marker formulation according to claim 1 wherein the barium sulfate and is administered in an amount less than 7.5 g per dose.

3. A liquid stool marker formulation according to claim 1 wherein barium sulfate is present in an amount of 5 g per dose.

4. A liquid stool marker formulation according to claim 3 wherein the barium sulfate is present in an amount greater than 1 g per dose.

5. A liquid stool marker formulation according to claim 1 wherein the barium sulfate has a particle size of about 3 microns.

6. A liquid stool marker formulation according to claim 1 wherein the flocculant is smectite clay.

7. A liquid stool marker formulation according to claim 1 further including a viscosity modifier which does not behave as a protective colloid in respect of the material to render stool opaque to radiation.

8. A liquid stool marker formulation according to claim 1 further including an anti-caking agent.

9. A liquid stool marker formulation according to claim 1 further treated with a treatment selected from the group consisting of high shear stirring and sonification prior to administration to a patient.

10. A liquid stool marker formulation according to claim 1 wherein the material to render stool opaque to radiation is present in an amount effective to differentiate stool from non-stool without rendering density or movement induced artefacts in a CT rendering of the stool.

11. A liquid stool marker formulation according to claim 1 including (% by weight):

| | |
| --- | --- |
| Barium Sulfate | 1.2% |
| Citric Acid Anhydrous | 0.03% |
| Hydroxypropyl methylcellulose | 0.45% |
| Smectite Clay | 0.75% |
| Flavour, Sweetener, Preservatives | q.s. |
| Water | q.s. 100%. |

12. A liquid stool marker formulation according to claim 1 prepared from a solid composition.

13. A method of radiologically visualising the colon of a patient including the steps of:

orally administering to a patient a stool marker formulation according to claim 1 to render stool opaque to radiation;

radiologically scanning the colon of the patient to produce data; and manipulating the data to determine that portion of the data due to marked stool, to thereby provide a representation of the colon, including where present, a polyp.

14. A method according to claim 13 wherein the radiological visualisation is by means of a CT scanner.

15. A method according to claim 13 wherein the radiological visualisation is by means of a helical scanner.

16. A method according to claim 13 wherein the manipulation of the data involves subtraction of that portion of the data due to the marked stool, leaving a representation of the colon, including where present a polyp.

17. A method of preparing a patient for a radiological examination including the step of administering to the patient a formulation according to claim 1 to render stool opaque to radiation.

18. A method according to claim 13 wherein the formulation is administered orally over 24 to 48 hours preceding the radiological examination.

19. A method according to claim 13 wherein the formulation is administered in four or more dosages over 24 to 48 hours preceding the radiological examination.

* * * * *

UNITED STATES PATENT AND TRADEMARK OFFICE
CERTIFICATE OF CORRECTION

PATENT NO. : 6,726,896 B2
APPLICATION NO. : 09/800076
DATED : April 27, 2004
INVENTOR(S) : Tait It is certified that error appears in the above-identified patent and that said Letters Patent is hereby corrected as shown below:

Column 4, line 11, "die" should read --the--;

Column 5, line 21, "trough" should read --through--;

Column 6, line 22, "formations" should read --functions--;

Column 7, line 1, "bydrocolloids" should read --hydrocolloids--;

Column 7, line 17, "dispersals" should read --dispersants--;

Column 8, line 57, "os" should read --of--; and

Column 8, line 59, "od" should read --of--.

Signed and Sealed this

Eighth Day of August, 2006

JON W. DUDAS
*Director of the United States Patent and Trademark Office*